United States Patent
Ivanov et al.

(10) Patent No.: US 8,642,797 B2
(45) Date of Patent: Feb. 4, 2014

(54) AMIDATE PRECURSORS FOR DEPOSITING METAL CONTAINING FILMS

(75) Inventors: Sergei Vladimirovich Ivanov, Schnecksville, PA (US); Wade Hampton Bailey, III, Emmaus, PA (US); Xinjian Lei, Vista, CA (US); Daniel P. Spence, Carlsbad, CA (US)

(73) Assignee: Air Products and Chemicals, Inc., Allentown, PA (US)

(*) Notice: Subject to any disclaimer, the term of this patent is extended or adjusted under 35 U.S.C. 154(b) by 249 days.

(21) Appl. No.: 13/030,227

(22) Filed: Feb. 18, 2011

(65) Prior Publication Data

US 2012/0045589 A1 Feb. 23, 2012

Related U.S. Application Data

(60) Provisional application No. 61/307,962, filed on Feb. 25, 2010.

(51) Int. Cl.
| | |
|---|---|
| C07F 7/00 | (2006.01) |
| C07F 11/00 | (2006.01) |
| C07F 15/00 | (2006.01) |
| C23C 16/00 | (2006.01) |

(52) U.S. Cl.
USPC .......... 556/56; 556/42; 556/45; 556/57; 556/146; 534/15; 427/248.1; 427/255.7; 427/569; 427/582

(58) Field of Classification Search
USPC ............. 556/56, 42, 45, 57, 146; 427/248.1, 427/255.7, 569, 582; 534/15
See application file for complete search history.

(56) References Cited

PUBLICATIONS

Dennes et al., Journal of American Chemical Society, vol. 129, No. 1, pp. 93-97 (2007).*
Pothiraja et al., Chemical Communications, Issue 15, pp. 1978-1980 (published on the Web Feb. 3, 2009).*
Garth R. Giesbrecht, et al, Synthesis and Structure of a Linked-Bis(amidate) Ligand and Some Complexes with Titanium, Inorganic Chemistry, 2001, vol. 40, pp. 6069-6072.
Robert K. Thomson, et al, Structure, Bonding, and Reactivity of Ti and Zr Amidate Complexes: DFT and X-Ray Crystallographic Studies, Inorganic Chemistry, 2005, vol. 44, pp. 8680-8689.
Patrick Eisenberger, et al, Tantalum-Amidate Complexes for the Hydroaminoalkylation of Secondary Amines: Enhanced Substrate Scope and Enantioselective Chiral Amine Synthesis, Angewandte Chemie Int. Ed., 2009, vol. 48, pp. 8361-8365.
Chunyu Li, et al, Amidate Complexes of Titanium and Zirconium: A New Class of Tunable Precatalysts for the Hydroamination of Alkynes, Chem. Commun., 2003, pp. 2462-2463.
Mahesh C. Karunarathne, Development of a New Class of Copper(III) Precursors for Use in Atomic Layer Deposition Film Growth—INOR 553, 236th ACS National Meeting, Philadelphia, PA, Aug. 17-21, 2008.

(Continued)

*Primary Examiner* — Porfirio Nazario Gonzalez
(74) *Attorney, Agent, or Firm* — Rosaleen P. Morris-Oskanian

(57) ABSTRACT

Volatile metal amidate metal complexes are exemplified by bis(N-(tert-butyl)ethylamidate)bis(ethylmethylamido) titanium; (N-(tert-butyl)(tert-butyl)amidate)tris(ethylmethylamido) titanium; bis(N-(tert-butyl)(tert-butyl)amidate)bis(dimethylamido) titanium and (N-(tert-butyl)(tert-butyl)amidate)tris(dimethylamido) titanium. The term "volatile" refers to any precursor of this invention having vapor pressure above 0.5 torr at temperature less than 200° C. Metal-containing film depositions using these metal amidate ligands are also described.

27 Claims, 7 Drawing Sheets

(56) References Cited

PUBLICATIONS

Zhe Zhang, et al, An Easy-To-Use, Regioselective, and Robust Bis(amidate) Titanium Hydroamination Precatalyst: Mechanistic and Synthetic Investigations Toward The Preparation of Tetrahydroisoquinolines and Benzoquinolizine Alkaloids, Chemistry—A European Journal, 2007, vol. 13., pp. 2012-2022.

David C. Leitch, et al, N, O-Chelates of Group 4 Metals: Contrasting The Use of Amidates and Ureates in The Synthesis of Metal Dichlorides, European Journal of Inorganic Chemistry, 2009, pp. 2691-2701.

Louisa J. E. Stanlake et al, Rare-Earth Amidate Complexes. Easily Accessed Initiators for E-Caprolactone Ring-Opening Polymerization, Inorganic Chemistry, 2008, vol. 47, pp. 8062-8068.

Louisa J. E. Stanlake, et al, Bis-and Mono(amidate) Complexes of Yttrium: Synthesis, Characterization, and Use As Precatalysts for the Hydroamination of Aminoalkenes, Organometallics, 2009, vol. 28, pp. 3990-3998.

Robert K. Thomson, et al, A Pentagonal Pyramidal Zirconium Imido Complex for Catalytic Hydroamination of Unactivated Alkenes, Organometallics, 2006, vol. 25, pp. 4069-4071.

* cited by examiner

AMIDATE PRECURSORS FOR DEPOSITING METAL CONTAINING FILMS

CROSS REFERENCE TO RELATED APPLICATION

The present patent application claims the benefit of prior U.S. Provisional Patent Application Ser. No. 61/307,962 filed Feb. 25, 2010.

BACKGROUND OF THE INVENTION

There is an ongoing search for precursors for deposition of metal containing films on various substrates. Metal containing films are used, for example, in gate dielectrics, capacitor dielectrics, electrode layers, seed layers and for many other functions in integrated circuit devices and microelectronic devices. Many precursors are known for vapor deposition of metal containing films, but new precursors are needed to improve precursor delivery process, for example to reduce clogging of the delivery lines and to reduce the formation of unwanted particles on the wafers, to increase deposition rate and deposition temperature and/or to improve the desired properties of metal containing films. For example, there is still a need to develop new Group 4 precursors, preferably liquid Group 4 precursors, which exhibit at least one of the following properties: lower molecular weight (e.g., 550 m.u. or below), lower melting point (e.g., 100° C. or below), and higher vapor pressure (e.g., 0.5 torr or greater at temperature less than 200° C.).

The following references are in the field of precursors for deposition of metal containing films and metal complexes containing amidate ligands.

"Development of a new class of copper(II) precursors for use in atomic layer deposition film growth"; Karunarathne, Mahesh C.; Heeg, Mary Jane; Winter, Charles H.; Abstracts of Papers, 236th ACS National Meeting, Philadelphia, Pa., United States, Aug. 17-21, 2008 (2008), INOR-553; Publisher: American Chemical Society, Washington, D.C.

"N,O-Chelates of Group 4 Metals: Contrasting the Use of Amidates and Ureates in the Synthesis of Metal Dichlorides"; Leitch, David C.; Beard, J. David; Thomson, Robert K.; Wright, Vincent A.; Patrick, Brian O.; Schafer, Laurel L Vancouver, European Journal of Inorganic Chemistry (2009), (18), pp 2691-2701.

"An Easy-To-Use, Regioselective, And Robust Bis(Amidate) Titanium Hydroamination Precatalyst: Mechanistic And Synthetic Investigations Toward The Preparation Of Tetrahydroisoquinolines And Benzoquinolizine Alkaloids"; Zhang, Zhe; Leitch, David C.; Lu, Man; Patrick, Brian O.; Schafer, Laurel L Vancouver, Chemistry—A European Journal (2007), 13 (7), pp 2012-2022.

"A Pentagonal Pyramidal Zirconium Imido Complex for Catalytic Hydroamination of Unactivated Alkenes"; Thomson, Robert K.; Bexrud, Jason A.; Schafer, Laurel L.; Organometallics (2006), 25 (17), pp 4069-4071

"Structure, Bonding, and Reactivity of Ti and Zr Amidate Complexes: DFT and X-Ray Crystallographic Studies"; Thomson, Robert K.; Zahariev, Federico E.; Zhang, Zhe; Patrick, Brian O.; Wang, Yan Alexander; Schafer, Laurel L.; Inorganic Chemistry (2005), 44 (24), pp 8680-8689.

"Amidate complexes of titanium and zirconium: a new class of tunable precatalysts for the hydroamination of alkynes"; Li, Chunyu; Thomson, Robert K.; Gillon, Bronwyn; Patrick, Brian O.; Schafer, Laurel L.; Chemical Communications (Cambridge, United Kingdom) (2003), (19), pp 2462-2463.

"Bis- and mono(amidate) complexes of yttrium: Synthesis, characterization, and use as precatalysts for the hydroamination of aminoalkenes."; Stanlake, L. J. E. and L. L. Schafer (2009). Organometallics 28 (14): pp 3990-3998.

"Tantalum-amidate complexes for the hydroaminoalkylation of secondary amines: enhanced substrate scope and enantioselective chiral amine synthesis"; Eisenberger, P., R. O. Ayinla, J. M. P. Lauzon and L. L. Schafer (2009). Angewandte Chemie—International Edition 48 (44): pp 8361-8365.

"Rare-earth amidate complexes. Easily accessed initiators for μ-caprolactone ring-opening polymerization"; Stanlake, L. J. E., J. D. Beard and L. L. Schafer (2008). Inorganic Chemistry 47 (18): pp 8062-8068.

"Synthesis and structure of a linked-bis(amidate) ligand and some complexes with titanium"; Giesbrecht, G. R., A. Shafir and J. Arnold (2001). Inorganic Chemistry 40 (23): pp 6069-6072.

BRIEF SUMMARY OF THE INVENTION

The present invention is methods and volatile precursors for forming a metal-containing film on a substrate using a vapor deposition process. Metal-containing precursors are represented by the following formula:

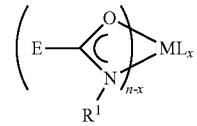

where M is selected from the Group 2 to Group 15 metal, including titanium, zirconium, hafnium, vanadium, niobium, tantalum, chromium, molybdenum, tungsten, lanthanide metals, calcium, strontium, barium, manganese, cobalt, nickel, iron and combinations thereof; $R^1$ is selected from the group consisting of linear or branched alkyl group containing 1 to 6 carbon atom, linear or branched alkoxyalkyl, linear or branched aminoalkyl, aryl group or alkyl-substituted aryl; E is $R^2$ or $NR^3R^4$, where $R^2$, $R^3$, $R^4$ are independently selected from the group consisting of linear or branched alkyl group containing 1-6 carbon atoms, cyclic alkyl groups of 4-6 carbon atoms, aryl groups of 6-12 carbon atoms or alkyl-substituted aryl group; L is an anionic ligand independently selected from alkoxy, dioxy, amido, diketonate, ketoiminate, diiminate, cyclopentadienyl, alkyl substituted cyclopentadienyl, alkoxysubstituted cyclopentadienyl, aminosubsitituted cyclopentadienyl, pyrrolyl, alkyl substituted pyrrolyl, alkoxysubstituted pyrrolyl, aminosubsitituted pyrrolyl; n is the oxidation state of M and x is 0 to n−1.

DETAILED DESCRIPTION OF THE INVENTION

Figure 1:
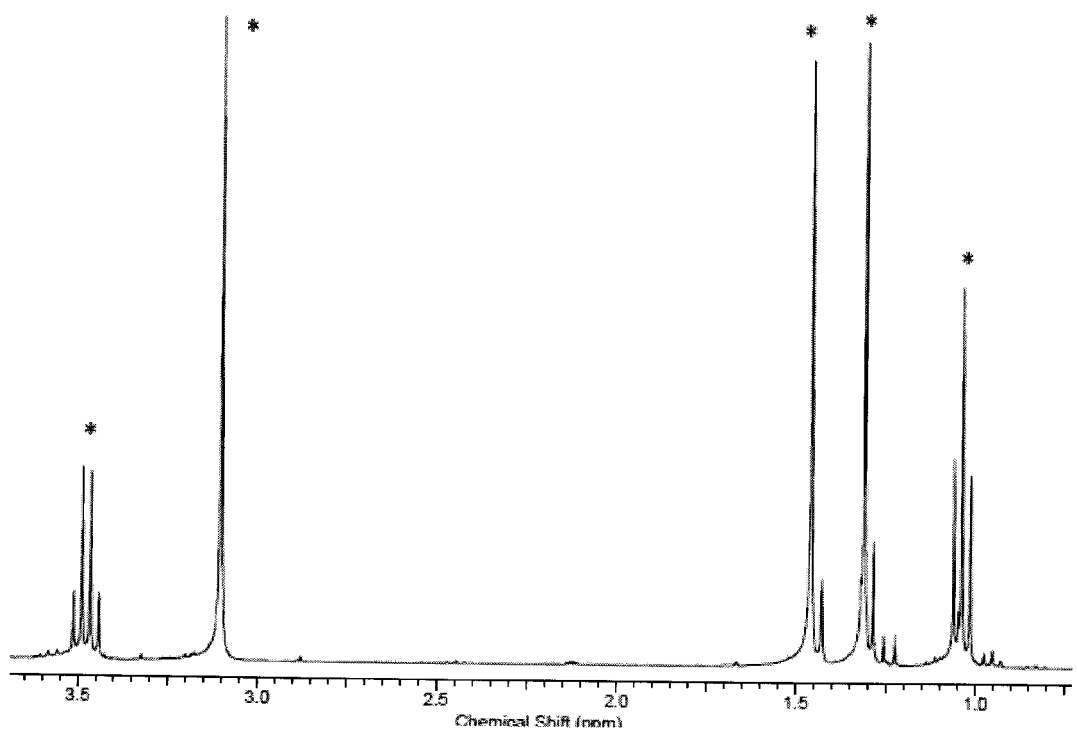
FIG. 1. [1]H nuclear magnetic resonance (NMR) spectrum of (N-(tert-butyl)(tert-butyl)amidate)tris(ethylmethylamido) titanium.

Disclosed herein are Group 2 to Group 15 volatile metal amidate complexes that are suitable, for example, as precursors in chemical vapor deposition processes. The complexes and compositions are useful for fabricating metal containing films on substrates such as silicon, metal nitride, metal oxide, metal oxynitride, metal silicate, and other metal containing layers via chemical vapor deposition (CVD), cyclic chemical vapor deposition (CCVD), atomic layer deposition (ALD) processes. As used herein, the term "volatile" referes to any precursor of this invention having vapor pressure above 0.5 torr at temperature less than 200° C. As used herein, the term "chemical vapor deposition processes" refers to any process wherein a substrate is exposed to one or more volatile precursors, which react and/or decompose on the substrate surface to produce the desired deposition. The deposited metal-containing films have applications ranging from computer chips, optical device, magnetic information storage, to metallic catalyst coated on a supporting material. In addition, metal complexes of this invention may also be used as catalysts for hydroamination, olefin polymerization and other applications.

Also disclosed herein are methods for preparing these complexes, as well as their use in vapor deposition processes, particularly CVD or atomic layer deposition (ALD) deposition processes. The family of precursors with amidate ligands is represented by the following Formula I:

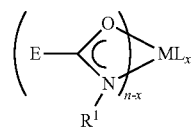

I where M is selected from the Group 2 to Group 15 metal, including titanium, zirconium, hafnium, vanadium, niobium, tantalum, chromium, molybdenum, tungsten, lanthanide metals, calcium, strontium, barium, manganese, cobalt, nickel, iron and combinations thereof; $R^1$ is selected from the group consisting of linear or branched alkyl group containing 1 to 6 carbon atom, linear or branched alkoxyalkyl, linear or branched aminoalkyl; E is $R^2$ or $NR^3R^4$, where $R^2$, $R^3$, $R^4$ are independently selected from the group consisting of linear or branched alkyl group containing 1-6 carbon atoms, cyclic alkyl groups of 4-6 carbon atoms and aromatic groups of 6-12 carbon atoms; L is an anionic ligand independently selected from alkoxy, dioxy, amido, diketonate, ketoiminate, diiminate, cyclopentadienyl, alkyl substituted cyclopentadienyl, alkoxysubstituted cyclopentadienyl, aminosubstituted cyclopentadienyl, pyrrolyl, alkyl substituted pyrrolyl, alkoxysubstituted pyrrolyl, aminosubstituted pyrrolyl; n is the oxidation state of M and x is 0 to n−1. For the purpose of the present invention, lanthanide metals shall mean lanthanum, cerium, praseodymium, neodymium, promethium, samarium, europium, gadolinium, terbium, dysprosium, holmium, erbium, thulium, ytterbium and lutetium.

Without being bound by any theory it is assumed that the amidate ligands used in the present invention can be coordinated to a metal in any of the three coordination modes shown below. Dynamic equilibrium may exist between these coordination modes in the liquid phase. For the purpose of the present invention, the depiction of Formula I above is deemed to include modes (a), (b) and (c), below.

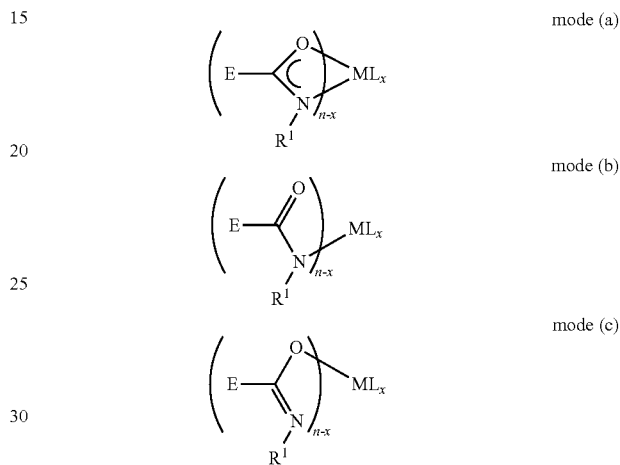

The term "alkyl" as used herein includes linear or branched alkyl groups, comprising from 1 to 10 carbon atoms, preferably from 1 to 6 carbon atoms, more preferably from 1 to 3 carbon atoms, alternately from 3 to 5 carbon atoms, further alternately from 4 to 6 carbons atoms, cyclic alkyl groups of 4-6 carbon atoms or variations of the foregoing ranges. Exemplary alkyl groups include, but are not limited to, methyl, ethyl, n-propyl, iso-propyl ($Pr^i$), n-butyl, iso-butyl, sec-butyl, tert-butyl ($Bu^t$), tert-amyl, n-pentyl, n-hexyl, cyclopentyl, and cyclohexyl. The term "alkyl" applies also to alkyl moieties contained in other groups such as haloalkyl, alkylaryl, or arylalkyl. The term "bulky" as used herein describes alkyl groups that are more sterically hindered compared to linear alkyl groups having the same number of carbon atoms and may include, for example, branched alkyl groups, cyclic alkyl groups, or alkyl groups having one or more side changes and/or substituents. The term "aryl" as used herein comprises 6 to 12 member carbon rings having aromatic character. Exemplary aryl groups include phenyl and napthyl groups. The term "alkyl-substituted aryl" applies to aryl moieties that are substituted with alkyl. Exemplary alkyl-substituted aryl groups include tolyl and xylyl groups. The term "halo" and "halogen" include fluorine, chlorine, bromine, or iodine. In certain embodiments, some of the groups discussed herein may be substituted with one or more other elements such as, for example, a halogen atom or other heteroatoms such as O, N, Si, or S. The term "alkoxy" as used herein includes linear, branched $C_{1-10}$ alkoxy, preferably $C_{1-6}$ alkoxy, or $C_{4-10}$ cyclic alkoxy. Exemplary alkoxy groups include, but are not limited to, methoxy, ethoxy, n-propoxy, iso-propoxy, n-butoxy, iso-butoxy, sec-butoxy, tert-butoxy, tert-amyloxy, n-pentoxy, n-hexoxy. The "term" amido as used below includes $NR^3R^4$, wherein $R^3$, $R^4$ are independently selected from the group consisting of $C_{1-6}$ linear or branched alkyl or $C_{4-6}$ cyclic alkyl or, aromatic groups; Exemplary amido groups include, but are not limited to, dimethylamido, diethylamido, ethylmethylamido.

In one particular embodiment, E is $R^2$, and $R^1$ and $R^2$ are independently selected from alkyl, aryl, or alkyl-substituted aryl, and the precursors are represented by the Formula II:

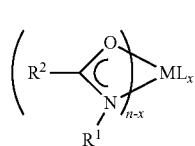

In certain embodiments, at least one of $R^1$ and $R^2$ in the amidate ligand of Formula II are different alkyl groups. In other embodiments, $R^1$ and $R^2$ in the amidate ligand are the same alkyl groups.

In another embodiment, amidate ligand is a polydentate ligand with pendant aminoalkyl group which may coordinate to a metal center. One type of the structure is illustrated in the structure III below.

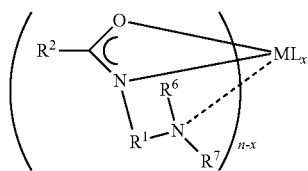

wherein M is selected from the Group 2 to Group 15 metal, including titanium, zirconium, hafnium, vanadium, niobium, tantalum, chromium, molybdenum, tungsten, lanthanide metals, calcium, strontium, barium, manganese, cobalt, nickel, iron and combination thereof; where $R^2$, $R^6$ and $R^7$ are independently selected from the group consisting of linear or branched alkyl group containing 1-6 carbon atoms, cyclic alkyl groups of 4-6 carbon atoms and aromatic groups of 6-12 carbon atoms, and $R^5$ is $C_{2-3}$ linear or branched alkylene bridge. L is an anionic ligand independently selected from alkoxy, amino, diketonate, ketoiminate, diiminate, cyclopentadienyl, alkyl substituted cyclopentadienyl, alkoxysubstituted cyclopentadienyl, aminosubsitituted cyclopentadienyl, pyrrolyl, alkyl substituted pyrrolyl, alkoxysubstituted pyrrolyl, aminosubsitituted pyrrolyl; n is the oxidation state of M and x is 0 to n−1.

In another embodiment, amidate ligand is a polydentate ligand with pendant alkoxyalkyl group which may coordinate to a metal center. One type of the structure is illustrated in the structure IV below

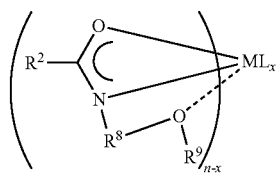

wherein M is selected from the Group 2 to Group 15 metal, including titanium, zirconium, hafnium, vanadium, niobium, tantalum, chromium, molybdenum, tungsten, lanthanide metals, calcium, strontium, barium, manganese, cobalt, nickel, iron and combination thereof; where $R^2$ and $R^9$ are independently selected from the group consisting of linear or branched alkyl group containing 1-6 carbon atoms, cyclic alkyl groups of 4-6 carbon atoms and aromatic groups of 6-12 carbon atoms, and $R^8$ is $C_{2-3}$ linear or branched alkylene bridge. L is an anionic ligand independently selected from alkoxy, amino, diketonate, ketoiminate, diiminate, cyclopentadienyl, alkyl substituted cyclopentadienyl, alkoxysubstituted cyclopentadienyl, aminosubsitituted cyclopentadienyl, pyrrolyl, alkyl substituted pyrrolyl, alkoxysubstituted pyrrolyl, aminosubsitituted pyrrolyl; n is the oxidation state of M and x is 0 to n−1.

In another embodiment, M is selected from the Group 4 metals comprising titanium, zirconium or hafnium and the complex is represented by the Formula V.

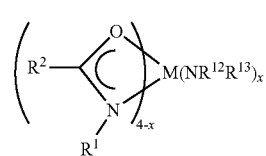

where $R^1$ and $R^2$ are independently selected from the group consisting of linear or branched alkyl group containing 1 to 6 carbon atom, linear or branched alkoxyalkyl, linear or branched aminoalkyl; $R^{12}$ and $R^{13}$ are independently selected from the group consisting of linear or branched alkyl group containing 1-6 carbon atoms, cyclic alkyl groups of 4-6 carbon atoms, preferably $R^3$ and $R^4$ are independently selected from methyl and ethyl groups; x is 0, 1, 2 or 3.

Specific examples are shown below, where amidate ligand can coordinate in a mono- or bi-dentate fashion.

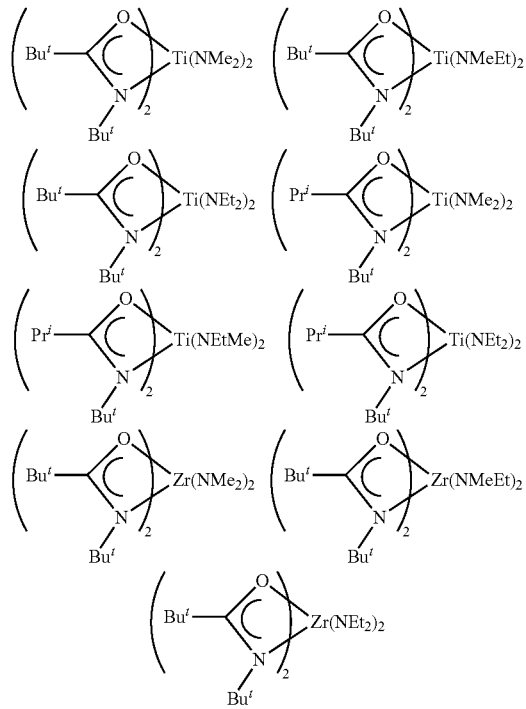

In another embodiment, M is selected from the Group 4 metal comprising titanium, zirconium or hafnium and the complex is represented by the Formula VI:

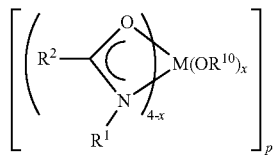

VI where $R^1$ and $R^2$ are independently selected from the group consisting of linear or branched alkyl group containing 1 to 6 carbon atom, linear or branched alkoxyalkyl, linear or branched aminoalkyl; $R^{10}$ is selected from the group consisting of linear or branched alkyl group containing 1-6 carbon atoms or cyclic alkyl groups of 4-6 carbon atoms; x is 0, 1, 2 or 3; p=1 or 2. $R^1$, $R^2$ and $R^{10}$ can more specifically independently be methyl, ethyl, n-propyl, iso-propyl, n-butyl, iso-butyl, sec-butyl, tert-butyl, and tert-amyl.

Specific examples are shown below where amidate ligand can coordinate in a mono- or bi-dentate fashion, and the structures can be monomeric or dimeric.

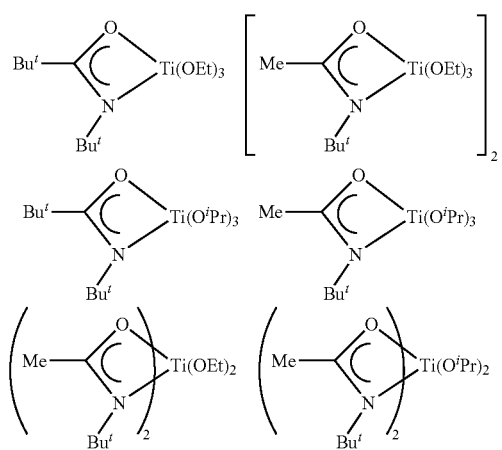

In another embodiment, M is selected from the Group 3 metals comprising scandium, yttrium and lanthanide metals, including lanthanum, cerium, europium, gadolinium, erbium, ytterbium and lutetium, and represented by Formula VII:

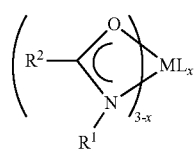

VII where $R^1$ and $R^2$ are independently selected from the group consisting of linear or branched alkyl group containing 1 to 6 carbon atom, linear or branched alkoxyalkyl, linear or branched aminoalkyl; L is an anionic ligand independently selected from alkoxy, amido, diketonate, ketoiminate, diiminate, cyclopentadienyl, alkyl substituted cyclopentadienyl, alkoxysubstituted cyclopentadienyl, aminosubstituted cyclopentadienyl, pyrrolyl, alkyl substituted pyrrolyl, alkoxysubstituted pyrrolyl, aminosubsitituted pyrrolyl; x is 0, 1 or 2.

In another embodiment, M is an alkaline earth metal and the complex is represented by the Formula VIII:

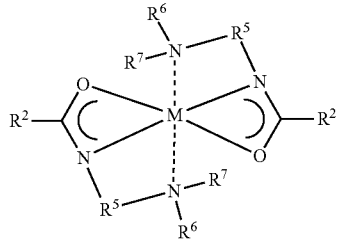

VIII where M is selected from calcium, strontium or barium; where $R^2$, $R^6$ and $R^7$ are independently selected from the group consisting of linear or branched alkyl group containing 1-6 carbon atoms, cyclic alkyl groups of 4-6 carbon atoms, aromatic groups of 6-12 carbon atoms, and $R^5$ is a linear or branched alkylene bridge, preferably ethylene or propylene group.

In another embodiment, M is an alkaline earth metal and the complex is represented by the Formula IX:

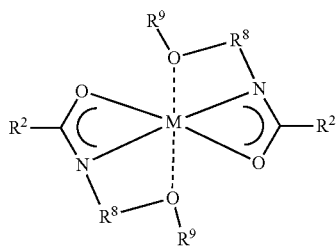

IX where M is selected from calcium, strontium or barium; where $R^2$ and $R^9$ are independently selected from the group consisting of linear or branched alkyl group containing 1-6 carbon atoms, cyclicalkyl groups of 4-6 carbon atoms and aromatic groups of 6-12 carbon atoms, and $R^8$ is a linear or branched alkylene bridge, preferably ethylene or propylene group.

In another embodiment, the precursor is represented by formula X:

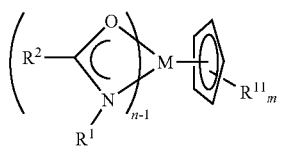

X where M is selected from a Group 2 to Group 15 metal, including titanium, zirconium, hafnium, vanadium, niobium, tantalum, chromium, molybdenum, tungsten, lanthanide metals, calcium, strontium, barium, manganese, cobalt, nickel, iron and combination thereof; $R^{1, 2\ \&\ 11}$ are independently selected from the group consisting of linear or branched alkyl group containing 1 to 6 carbon atom, linear or branched alkoxyalkyl, linear or branched aminoalkyl, m=0, 1, 2, 3, 4, 5 and n is the oxidation state of M. Specifically, $R^{1, 2, \& 11}$ are preferably independently selected from the group consisting of methyl (Me), ethyl (Et), n-propyl, iso-propyl ($Pr^i$), n-butyl, isobutyl, sec-butyl, and ter-butyl ($Bu^t$).

Specific examples are shown below where amidate ligand can coordinate in a mono- or bi-dentate fashion.

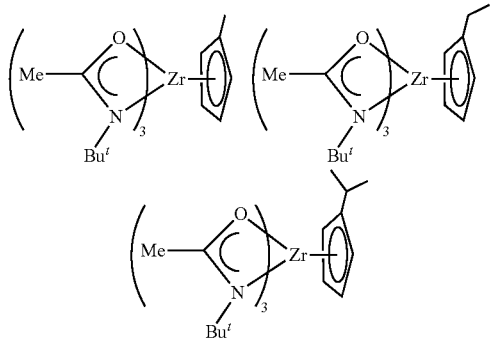

In another embodiment, the precursor is a liquid or low melting point solid which exhibits at least one of the following properties: low molecular weight (e.g., 550 m.u. or below), low viscosity (600 cP and below), low melting point (e.g., 100° C. or below), and high vapor pressure (e.g., 0.5 torr or greater at temperature less than 200° C.).

The amidate ligands can be prepared by well known procedures from acid chlorides and amines, as illustrated below:

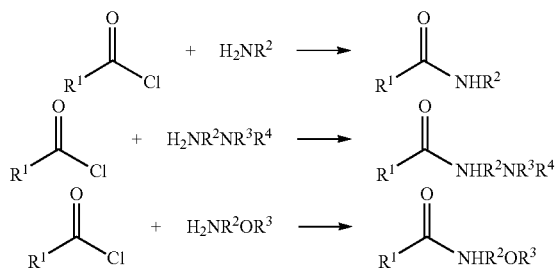

The metal complexes of this invention can be prepared by protonolysis reaction wherein organic amide is reacted with a metal complex containing ligands more basic than the organic amide, and thus capable abstracting proton from the organic amide. One type of this reaction is represented by the reaction below:

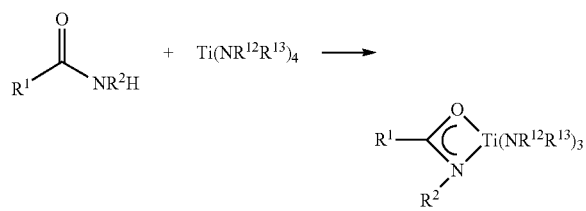

The metal complexes of this invention can also be prepared by metathesis reaction of metal halide complex with lithium amidate.

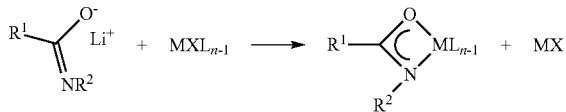

Also described herein is a method for making metal-containing oxide film, metal-containing nitride film, metal-containing oxynitride film, metal-containing silicate film, multi-component metal oxide film, and any combination or laminate thereof, which may be used, for example, in fabricating semiconductor devices. In one embodiment, the method disclosed herein provides a Group 4 metal or multi-component metal oxide film that has a dielectric constant substantially higher than that of either conventional thermal silicon oxide, silicon nitride, or zirconium/hafnium oxide dielectric.

The method disclosed herein deposits the metal containing films using atomic layer deposition (ALD) or chemical vapor deposition (CVD) processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via plasma enhanced ALD (PEALD) or plasma enhanced cyclic CVD (PECCVD) process. In these embodiments, the deposition temperature may be relatively lower, or may range from 150° C. to 600° C., and may allow for a wider process window to control the specifications of film properties required in end-use applications. Exemplary deposition temperatures for the PEALD or PECCVD deposition include ranges having any one or more of the following endpoints: 175, 200, 225, 250, 275, 300, 325, 350, 375, and/or 400° C.

In one embodiment of the method disclosed herein, a metal silicate or metal silicon oxynitride film is formed onto at least one surface of a substrate using metal-containing precursor having Formula I, a silicon-containing precursor, an oxygen source, and optionally a nitrogen source. Although metal-containing and silicon-containing precursors typically react in either liquid form or gas phase thereby preventing film formation, the method disclosed herein avoids pre-reaction of the metal containing and silicon-containing precursors by using ALD or CCVD methods that separate the precursors prior to and/or during the introduction to the reactor.

In this connection, deposition techniques such as an ALD or CCVD processes are used to deposit the metal-containing film. For example, in certain embodiments, an ALD process is used to deposit the metal-containing film. In a typical ALD process, the film is deposited by exposing the substrate surface alternatively to the metal precursor or the silicon-containing precursors. Film growth proceeds by self-limiting control of surface reaction, the pulse length of each precursor, and the deposition temperature. However, once the surface of the substrate is saturated, the film growth ceases.

In yet another embodiment, the metal-containing film may be deposited using a CCVD process. In this embodiment, the CCVD process may be performed using a higher temperature range than the ALD window, or from 350° C. to 600° C. Exemplary deposition temperatures for the CCVD deposition include ranges having any one or more of the following end points (provided in degrees Celsius): 200, 225, 250, 275, 300, 325, 350, 375, 400, 425, 450, 475, 500, 525, 550, 575, and/or 600° C.

As mentioned previously, the method disclosed herein forms the metal-containing films using at least one metal precursor having formula I described herein, optionally at least one silicon-containing precursor, optionally an oxygen source, optionally an additional metal-containing or other metal-containing precursor precursor, optionally a reducing agent, and optionally a nitrogen source. Although the precursors and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator.

In certain embodiments, other metal-containing precursors can be used in addition to the metal-containing precursors described herein. Metals commonly used in semiconductor fabrication include that can be used as the metal component for the metal amide includes: titanium, tantalum, tungsten, hafnium, zirconium, cerium, zinc, thorium, bismuth, lanthanum, strontium, barium, lead, and combinations thereof. Examples of other metal-containing precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino) hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino) tantalum (TBTDET), tert-butylimino tri(dimethylamino) tantalum (TBTDMT), tert-butylimino tri(ethylmethylamino) tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis (diethylamino)tungsten, bis(tert-butylimino)bis (ethylmethylamino)tungsten, bis(2,2,6,6-tetramethyl-3,5-heptanedionato)strontium, bis(2,2,6,6-tetramethyl-3,5-heptanedionato)barium, $M(R_nC_5H_{5-n})_2$, wherein n=1-5, R is selected from linear or branched $C_{1-6}$ alkyls; $M(R_nC_4NH_{4-n})_2$, wherein n=2-4, R is selected from linear or branched $C_{1-6}$ alkyls, and $M(R_nN_2H_{3-n})_2$m where n=2-3, R is selected from linear or branched $C_{1-6}$ alkyls, and combinations thereof.

In embodiments wherein the metal film deposited is a metal silicate, the deposition process further involves the introduction of at least one silicon-containing precursor. Examples of suitable silicon-containing precursors include a monoalkylaminosilane precursor, a hydrazinosilane precursor, or combinations thereof. In certain embodiments, the silicon-containing precursor comprises a monoalkylaminosilane precursor having at least one N—H fragment and at least one Si—H fragment. Suitable monoalkylaminosilane precursors containing both the N—H fragment and the Si—H fragment include, for example, bis(tert-butylamino)silane (BTBAS), tris(tert-butylamino)silane, bis(iso-propylamino) silane, tris(iso-propylamino)silane, and mixtures thereof. In one embodiment, the monoalkylaminosilane precursor has the formula $(R^7NH)_nSiR^8_mH_{4(n+m)}$ wherein $R^7$ and $R^8$ are the same or different and independently selected from the group consisting of alkyl, vinyl allyl, phenyl, cyclic alkyl, fluoroalkyl, and silylalkyl and wherein n is a number ranging from 1 to 3, m is a number ranging from 0 to 2, and the sum of "n+m" is a number that is less than or equal to 3. In another embodiment, the silicon-containing precursor comprises a hydrazinosilane having the formula $(R^9_2N-NH)_xSiR^{10}_yH_{4(x+y)}$ wherein $R^9$ and $R^{10}$ are same or different and independently selected from the group consisting of alkyl, vinyl, allyl, phenyl, cyclic alkyl, fluoroalkyl, silylalkyls and wherein x is a number ranging from 1 to 2, y is a number ranging from 0 to 2, and the sum of "x+y" is a number that is less than or equal to 3. Examples of suitable hydrazinosilane precursors include, but are not limited to, bis(1,1-dimethylhydrazino)-silane, tris(1,1-dimethylhydrazino)silane, bis(1,1-dimethylhydrazino)ethylsilane, bis(1,1-dimethylhydrazino)isopropylsilane, bis(1,1-dimethylhydrazino) vinylsilane, and mixtures thereof. Depending upon the deposition method, in certain embodiments, the silicon-containing precursor may be introduced into the reactor at a predetermined molar volume, or from about 0.1 to about 1000 micromoles. In this or other embodiments, the silicon-containing precursor may be introduced into the reactor for a predetermined time period, or from about 0.001 to about 500 seconds. The silicon-containing precursors react with the metal hydroxyl groups formed by the reaction of the metal amide with the oxygen source and become chemically adsorbed onto the surface of the substrate which results in the formation of a silicon oxide or a silicon oxynitride via metal-oxygen-silicon and metal-oxygen-nitrogen-silicon linkages, thus providing the metal silicate or the metal silicon oxynitride film.

As previously mentioned, some of the films deposited using the methods described herein (e.g., metal silicate or the metal silicon oxynitride films) may be formed in the presence of oxygen. An oxygen source may be introduced into the reactor in the form of at least one oxygen source and/or may be present incidentally in the other precursors used in the deposition process. Suitable oxygen source gases may include, for example, water ($H_2O$) deionized water, purifier water, and/or distilled water), water plasma, oxygen ($O_2$), oxygen plasma, ozone ($O_3$), NO, $NO_2$, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In this or other embodiments wherein the film is deposited by an ALD process, the precursor pulse can have a pulse duration that is greater than 0.01 seconds, and the oxidant pulse duration can have a pulse duration that is greater than 0.01 seconds, while the water pulse duration can have a pulse duration that is greater than 0.01 seconds. In yet another embodiment, the purge duration between the pulses that can be as low as 0 seconds.

The deposition methods disclosed herein may involve one or more purge gases. The purge gas, which is used to purge away unconsumed reactants and/or reaction byproducts, is an inert gas that does not react with the precursors and may preferably be selected from the group consisting of Ar, $N_2$, He, $H_2$ and mixture thereof. In certain embodiments, a purge gas such as Ar is supplied into the reactor at a flow rate ranging from about 10 to about 2000 sccm for about 0.1 to 1000 seconds, thereby purging the unreacted material and any byproduct that remain in the reactor.

In certain embodiments, such as, for example, for those embodiments where a metal silicon oxynitride film is deposited, an additional gas such as a nitrogen source gas may be introduced into the reactor. Examples of nitrogen source gases may include, for example, NO, $NO_2$, ammonia, hydrazine, monoalkylhydrazine, dialkylhydrazine, and combinations thereof.

In one embodiment of the method described herein, the temperature of the substrate in the reactor, i.e., a deposition chamber, is about 600° C. or below or about 500° C. or below or from 250 to 400° C. In this or other embodiments, the pressure may range from about 0.1 Torr to about 100 Torr or from about 0.1 Torr to about 5 Torr.

The respective step of supplying the precursors, the oxygen source, and/or other precursors or source gases may be performed by changing the time for supplying them to change the stoichiometric composition of the resulting metal silicate, metal silicon oxynitride film, or other metal-containing film.

Energy is applied to the at least one of the precursor, oxygen source gas, reducing agent, or combination thereof to induce reaction and to form the metal-containing film on the substrate. Such energy can be provided by, but not limited to, thermal, plasma, pulsed plasma, helicon plasma, high density plasma, inductively coupled plasma, X-ray, e-beam, photon, and remote plasma methods. In certain embodiments, a secondary radio frequency (RF) frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

In yet another embodiment of the method disclosed herein, the metal-containing film is formed using a vapor deposition method that comprises the steps of: a. introducing a metal-containing precursor in a vapor state into a reaction chamber and chemisorbing the metal-containing precursor onto a substrate which is heated; b. purging away the unreacted metal-containing precursor; c. introducing an oxygen source onto the heated substrate to react with the sorbed metal-containing precursor; and d. purging away the unreacted oxygen source. The above steps define one cycle for the method described herein; and the cycle can be repeated until the desired thickness of a metal-containing film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and the oxygen source gases may be performed by varying the duration of the time for supplying them to change the stoichiometric composition of the resulting metal oxide film. For multicomponent metal oxide films, a strontium-containing precursor, a barium-containing precursor or both precursors can be alternately introduced in step a into the reactor chamber.

The metal-containing precursor and/or other metal containing precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Mn, to enable low volatility materials to be volumetrically delivered, leading to reproducible transport and deposition without thermal decomposition of the precursor. Both of these considerations of reproducible transport and deposition without thermal decomposition.

In one embodiment of the method described herein, a cyclic deposition process such as CCVD, ALD, or PEALD may be employed, wherein a metal-containing precursor or its solution and an oxygen source such as, for example, ozone, oxygen plasma or water plasma are employed. The gas lines connecting from the precursor canisters to the reaction chamber are heated to one or more temperatures ranging from about 50° C. to about 200° C. depending upon the process requirements, and the container of the Group 4 metal-containing precursor is kept at one or more temperatures ranging from about 50° C. to about 190° C. for bubbling whereas the solution comprising the Group 4 metal-containing precursor is injected into a vaporizer kept at one or more temperatures ranging from about 50° C. to about 180° C. for direct liquid injection. A flow of 100 standard cubic centimeters per second (sccm) of argon gas may be employed as a carrier gas to help deliver the vapor of metal-containing precursor to the reaction chamber during the precursor pulsing. The reaction chamber process pressure is about 1 Torr. In a typical ALD or CCVD process, the substrate, such as silicon oxide or metal nitride, are heated on a heater stage in a reaction chamber that is exposed to the metal-containing precursor initially to allow the complex to chemically adsorb onto the surface of the substrate. An inert gas, such as argon gas, purges away unadsorbed excess complex from the process chamber. After sufficient Ar purging, an oxygen source is introduced into reaction chamber to react with the absorbed surface followed by another inert gas purge to remove reaction by-products from the chamber. The process cycle can be repeated to achieve the desired film thickness.

In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate. The solvent employed in solubilizing the precursor for use in a deposition process may comprise any compatible solvent or their mixture including aliphatic hydrocarbons (e.g., hexane, heptane, octane, and pentane), aromatic hydrocarbons (e.g., benzene or toluene), ethers, esters, nitriles, alcohols, amines (e.g., triethylamine, tert-butylamine), imines and carbodiimides (e.g., N,N'-diisopropylcarbodiimide), ketones, aldehydes, amidines, guanadines, isoureas, and the like. Further examples of suitable solvent are selected from the group consisting of glyme solvents having from 1 to 20 ethoxy —$(C_2H_4O)$— repeat units; organic ethers selected from the group consisting of propylene glycol groups; $C_2$-$C_{12}$ alkanols; organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines, polyamines, aminoethers and organic amides. Another class of solvents that offers advantages is the organic amide class of the form RCONR'R" wherein R and R' are alkyl having from 1-10 carbon atoms and they can be connected to form a cyclic group $(CH_2)_n$, wherein n is from 4-6, preferably 5, and R" is selected from alkyl having from 1 to 4 carbon atoms and cycloalkyl. N-methyl- or N-ethyl- or N-cyclohexyl-2-pyrrolidinones, N,N-Diethylacetamide, and N,N-Diethylformamide are examples.

The utility of specific solvent compositions for particular precursors may be readily empirically determined, to select an appropriate single component or multiple component solvent medium for the liquid delivery vaporization and transport of the specific amidate metal complex precursor that is employed.

In another embodiment, a direct liquid delivery method can be employed by dissolving the metal-containing precursor in a suitable solvent or a solvent mixture to prepare a solution with a molar concentration from 0.01 to 2 M, depending the solvent or mixed-solvents employed. The solvent employed herein may comprise any compatible solvents or their mixture including, but not limited to, aliphatic hydrocarbons, aromatic hydrocarbons, linear or cyclic ethers, esters, nitriles, alcohols, amines, polyamines, aminoethers and organic amides, preferably a solvent with a high boiling point, such as octane, decane, dodecane and dipropylene glycol dimethyl ether.

The method described herein also includes a cyclic deposition process for the formation of ternary metal oxide films wherein a plurality of precursors are sequentially introduced into a deposition chamber, vaporized and deposited on a substrate under conditions for forming a said ternary metal oxide film.

In one particular embodiment, the resultant metal oxide films can be exposed to a post-deposition treatment such as a plasma treatment to densify the film.

As mentioned previously, the method described herein may be used to deposit a metal-containing film on at least a portion of a substrate. Examples of suitable substrates include, but are not limited to, semiconductor materials such as strontium titanate, barium strontium titanate, yttrium oxide doped with titanium, lanthanum oxide doped with titanium, and other lanthanide oxides doped with titanium.

The following examples illustrate the methods for preparing Group 4 metal-containing precursors described herein are not intended to limit it in any way.

EXAMPLE 1

Synthesis of N-(tert-butyl)isopropylamide 250 ml RB flask equipped with stirring bar, overhead condenser, thermocouple and addition funnel was charged with 45 ml of anhydrous tetrahydrofuran (THF), 17.7 ml of $H_2N$—$C(CH_3)_3$ and 11.8 ml of triethylamine ($NEt_3$). The solution was cooled to 0° C. and 9.5 ml of isobutyryl chloride was added dropwise. After the addition was completed the very thick slurry was warmed up to RT and agitated for 1 hour. The slurry was diluted with diethyl ether (40 ml) and neutralized with ~75 ml of 1 M HCl. Organic layer was separated on the separatory funnel and aqueous fraction was washed with 40 ml of ether. Organic fractions were combined and dried over MgSO4. All volatiles were removed under vaccum using rotary evaporator and 12.3 g of white solid was collected. The solid was purified by sublimation under vacuum (100 mtorr) at 50-70° C. to collect 10.6 g of N-(tert-butyl)isopropylamide.

EXAMPLE 2

Synthesis of N-(tert-butyl)ethylamide 250 ml RB flask equipped with stirring bar, overhead condenser, thermocouple and addition funnel was charged with 75 ml of anhydrous THF, 22.7 ml of $H_2N$—$C(CH_3)_3$ and 15 ml of $NEt_3$. The solution was cooled to −30° C. and 9.5 ml of propionyl chloride was added dropwise within ~40 minutes. After the addition was completed the very thick slurry was warmed up to RT and agitated for 1 hour. The slurry was diluted with diethyl ether (40 ml) and neutralized with ~75 ml of 1 M HCl. Organic layer was separated on the separatory funnel and aqueous fraction was washed with 40 ml of ether. Organic fractions were combined and dried over MgSO4. All volatiles were removed under vaccum using rotary evaporator and 11.5 g of white solid was collected. The solid was purified by sublimation under vacuum (100 mtorr) at 60-70 C to collect 10.76 g of N-(tert-butyl)ethylamide.

EXAMPLE 3

Synthesis of N-(tert-butyl)(tert-butyl)amide

A dry, nitrogen-purged 500 ml 3-neck, round-bottom flask equipped with overhead mechanical stirrer, condenser, thermocouple, and 50 ml addition funnel was charged with 100 ml of anhydrous tetrahydrofuran, tert-butylamine (14.62 g, 0.200 mol), and triethylamine (10.12 g, 0.100 mol) using no-air syringe techniques. The solution was cooled to −30 C and trimethylacetyl chloride (10.00 g, 0.084 mol) in 20 ml tetrahydrofuran was added drop-wise from the addition funnel to the vigorously stirred solution. The reaction temperature was maintained at approximately −30 C during the addition as copious amounts of white precipitate are observed. After the addition was completed the reaction mixture was warmed up to 20° C. and agitated for 1 hour. The reaction mixture was diluted with 100 ml diethyl ether and treated with 100 ml of 1 M aqueous hydrochloric acid to neutralize residual amine and to extract amine salts into water fraction. The organic layer was separated and washed with 2×50 ml portions of 1 M NaOH followed by 2×50 ml portions of deionized water. The resulting product solution was dried over magnesium sulfate. The organic solvents were removed by rotary evaporation and the product was purified by vacuum transfer at 50° C./80 mmHg giving 12.28 g (93% yield) of a white solid which was analyzed by NMR [$^1$H-NMR ($d_8$-toluene) δ: 1.16 (9H, s, tert-butyl), 1.34 (9H, s, tert-butyl), 5.40 (1H, s, NH)]. The product is stored and used in a nitrogen-purged glove box.

EXAMPLE 4

Synthesis of bis(N-(tert-butyl)isopropylamidate)bis (diethylamido) Titanium 250 ml RB flask equipped with stirring bar, overhead condenser, thermocouple and addition funnel was charged with 1.42 g of N-(tert-butyl)isopropylamide (10 mmol) and 50 ml of anhydrous toluene. The solution of $Ti(NEt)_4$ (1.68 g, 5 mmol) in 20 ml of anhydrous toluene was added dropwise at −30° C. The reaction mixture was warmed up to RT and the solution became red-orange. The solution was heated to 80° C. for 1 hour, then cooled to 40° C. and toluene was distilled under vacuum. 2.2 g of red sticky solid was collected. The solid was purified by sublimation under vacuum (0.1 torr) at 160° C. to obtain 1.45 g of red solid. The complex was characterized by TGA, which shows that the complex is a volatile material.

EXAMPLE 5

Synthesis of bis(N-(tert-butyl)ethylamidate)bis(ethylmethylamido) Titanium

In nitrogen-purged glove box a 3-neck, 250 ml round bottom flask equipped with magnetic stir bar, vacuum distillation condenser, internal thermocouple and addition funnel was charged with N-(tert-butyl)ethylamide (1.29 g, 0.010 mol) and 50 ml of anhydrous toluene. Tetrakis(ethylmethylamido) titanium, or TEMAT (1.40 g, 0.005 mol) was charged to the addition funnel with 50 ml of anhydrous toluene. The flask was moved to a nitrogen purged schlenk line and cooled to −78° C. The solution of TEMAT was added drop-wise to the solution of amide precursor. Following the addition, the reaction was allowed to warm to room temperature during which a temperature change from yellow to red occurred at approximately −10° C. The resulting solution was agitated at 20° C. for 24 hours, then was heated to 80° C. for one hour. Toluene was then distilled at 40° C. under reduced pressure revealing a red, sticky solid. The crude product was partially sublimed (solid sublimate kept falling back into the bottom of the sublimator) at 130° C./80 mtorr to provide 1.20 g (62% isolated yield) of purified product [$^1$H-NMR (d$_8$-toluene) δ: 1.13 (6H, t, J=7.0 Hz, amido ethyl CH3), 1.18 (6H, t, J=7.6 Hz, carbonyl CH3), 1.25 (18H, s, tert-butyl), 2.12 (4H, q, J=7.6 Hz, carbonyl CH$_2$), 3.16 (4H, q, J=7.0 Hz, amido CH$_2$), 3.53 (6H, s, amido CH$_3$)].

EXAMPLE 6

Figure 2:
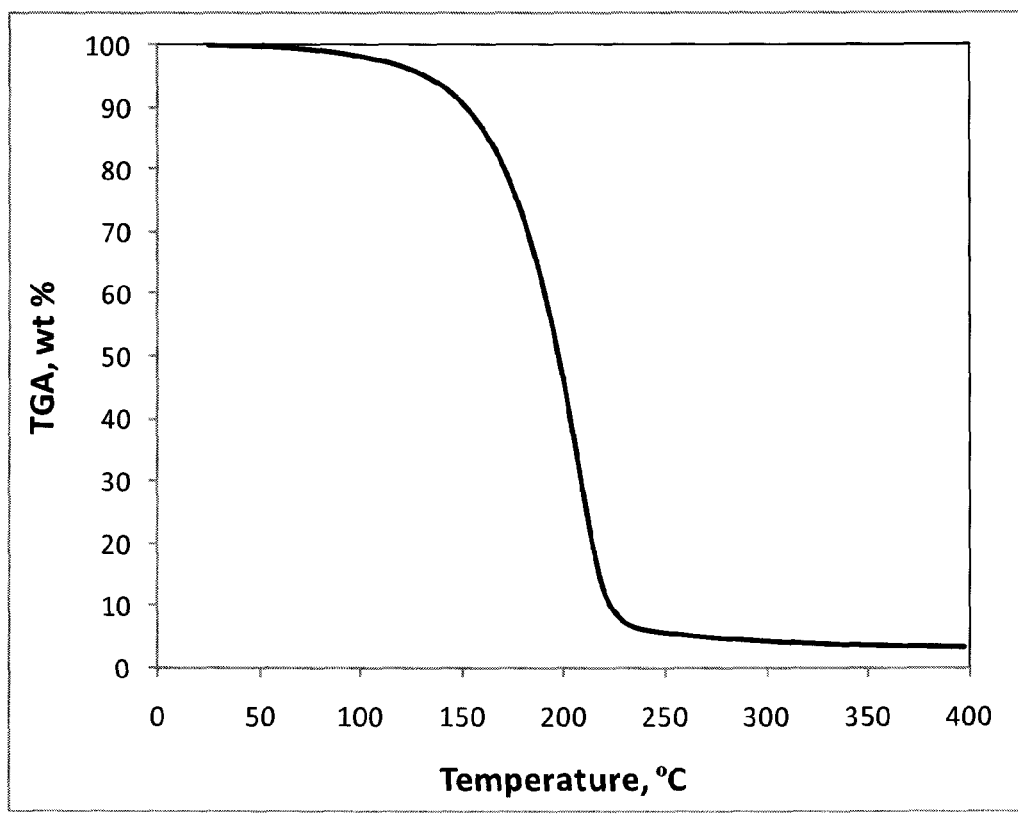
FIG. 2. Thermogravimetric Analysis (TGA) of of (N-(tert-butyl)(tert-butyl)amidate)tris(ethylmethylamido) titanium.

Synthesis of (N-(tert-butyl)(tert-butyl)amidate)tris (ethylmethylamido) Titanium In a nitrogen-purged glove box a 3-neck, 250 ml round bottom flask equipped with magnetic stir bar, vacuum distillation condenser, thermocouple, and addition funnel was charged with N-(tert-butyl)(tert-butyl)amide (1.57 g, 0.010 mol) and 50 ml of anhydrous toluene. Tetrakis(ethylmethylamido)titanium, or TEMAT (1.40 g, 0.005 mol) was charged to the addition funnel with 50 of anhydrous toluene. The flask was moved to a nitrogen purged schlenk line and cooled to −78° C. The solution of TEMAT was added drop-wise to the solution of the amide precursor. Following the addition the reaction mixture was warmed to 20° C. and held for 1 hour giving a light-yellow solution. The reaction mixture was then heated to 113° C. where the reaction mixture color changed to red and much of the toluene was distilled at atmospheric pressure. Residual toluene and amide precursor were removed at 50° C. under reduced pressure revealing a red, oily liquid. The crude product was partially purified (to avoid contamination of product at small scales) by vacuum transfer at 130° C./50 mtorr to provide 1.02 g (54% isolated yield) of the product in 96% purity by NMR analysis [$^1$H-NMR (d$_8$-toluene) δ: 1.04 (9H, t, J=7.2 Hz, ethyl amido CH3), 1.31 (9H, s, tert-butyl), 1.46 (9H, s, tert-butyl), 3.10 (9H, s, amido CH$_3$) 3.48 (6H, q, J=7.2 Hz, amido CH$_2$)].
TGA analysis shown in FIG. 2 indicates good volatility and low involatile residue, 3.3 wt %.

EXAMPLE 7

Synthesis of a Mixture of bis(N-(tert-butyl)(tert-butyl)amidate)bis(dimethylamido) Titanium and (N-(tert-butyl)(tert-butyl)amidate)tris(dimethylamido) Titanium In a nitrogen-purged glove box a 3-neck, 250 ml round bottom flask equipped with magnetic stir bar, vacuum distillation condenser, thermocouple and addition funnel was charged with N-(tert-butyl)(tert-butyl)amide (1.57 g, 0.010 mol) and 50 ml of anhydrous toluene. Tetrakis(dimethylamido)titanium, or TDMAT (1.12 g, 0.005 mol) was charged to the addition funnel with 50 of anhydrous toluene. The flask was moved to a nitrogen purged schlenk line and cooled to −78° C. The solution of TDMAT was added drop-wise to the solution of amide precursor. Following the addition the reaction mixture was allowed to warm to 20° C. and held for 1 hour. The reaction mixture was then heated to 113° C. where the color changed to red and much of the toluene was distilled at atmospheric pressure. Residual toluene and amide precursor were removed at 50° C. under reduced pressure revealing a red, oily liquid. The crude product was partially purified (to avoid contamination of product at small scales) by vacuum transfer at 120° C./50 mtorr to provide 1.50 g (67% isolated yield) of product represented as mixture of 45% (mole basis) (N-(tert-butyl)(tert-butyl)amidate)tris(dimethylamido)titanium [$^1$H-NMR (d$_8$-toluene) δ: 1.32 (9H, s, tert-butyl), 1.48 (9H, s, tert-butyl), 3.09 (18H, s, amido CH$_3$)] and 55% (mole basis) bis(N-(tert-butyl)(tert-butyl)amidate)bis(dimethylamido)titanium [$^1$H-NMR (d$_8$-toluene) δ: 1.29 (18H, s, tert-butyl), 1.44 (18H, s, tert-butyl), 3.08 (12H, s, amido CH$_3$)] by NMR analysis.

EXAMPLE 8

Synthesis of (N-(tert-butyl)(tert-butyl)amidate)tris (dimethylamido) Titanium

Figure 3:
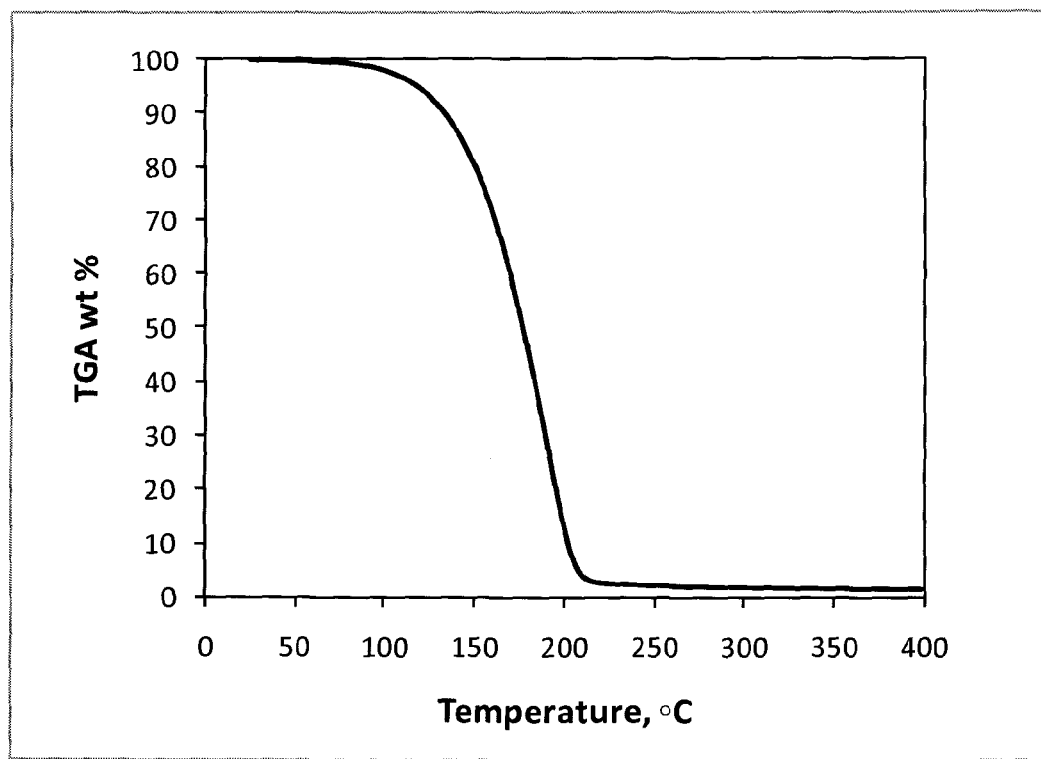
FIG. 3. TGA of (N-(tert-butyl)(tert-butyl)amidate)tris(dimethylamido) titanium.
Figure 4:
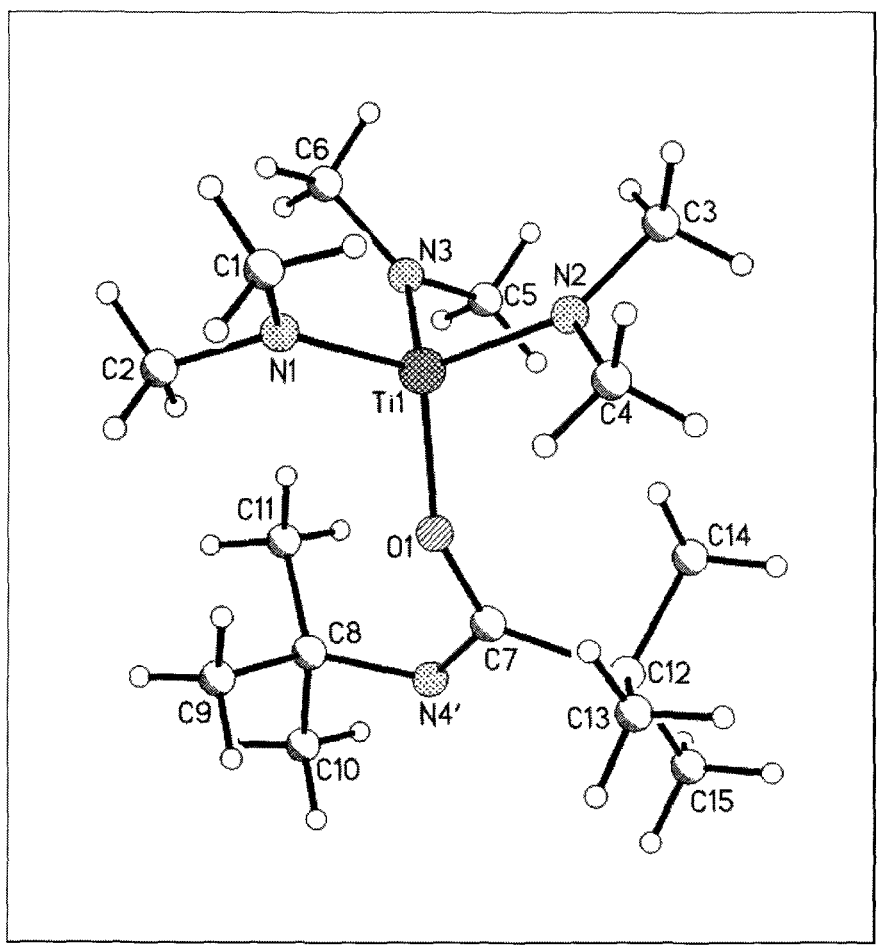
FIG. 4. Drawing representative of the crystal structure of (N-(tert-butyl)(tert-butyl)amidate)tris(dimethylamido) titanium showing monodentate binding mode for the amidate ligand, mode (c).

In a glove box, a 3-neck-250 ml RB flask equipped with magnetic stir bar, short-path vacuum distillation condenser, and a thermocouple was charged with 2.70 g (0.018 mol) N-t-butyl t-butyl amide and 30 ml of anhydrous toluene. 3.50 g (0.016 mol) Tetrakis-(dimethylamido) titanium (TDMAT) diluted in 20 ml of anhydrous toluene was added to the amide solution at 20° C. with mixing. The flask was moved to a nitrogen-purged Schlenk line and stirred at room temperature for 1 hour. The mixture was then heated to affect reactive distillation forcing over free amine and toluene until the distillation no longer progressed. Excess toluene and amide were removed at 60° C. under reduced pressure. Excess TDMAT was removed by initial vacuum distillation (65° C., 150 mTorr) and the product was vacuum distilled (83-85° C., 50 mtorr) providing 4.2 g (83% yield) of liquid (N-(tert-butyl)(tert-butyl)amidate)tris(dimethylamido) titanium containing less than 3 mol % of TDMAT. The product can be purified of TDMAT by treating further with a vacuum of <10 mTorr for an extended period of time. High purity (N-(tert-butyl)(tert-butyl)amidate)tris(dimethylamido) titanium is a dark-yellow solid at room temperature with a melting point of 28-29° C. [$^1$H-NMR (d$_8$-toluene) δ: 1.32 (9H, s, tert-butyl), 1.48 (9H, s, tert-butyl), 3.09 (18H, s, amido CH$_3$)].
TGA analysis shown in FIG. 3 indicates very good volatility and low involatile residue, 1.4 wt %. The vapor pressure of this precursor is estimated ~1 torr at 105° C.

EXAMPLE 9

Synthesis of tris(N-tert-butylacetamidate)ethylcyclopentadienyl Zirconium

Figure 5:
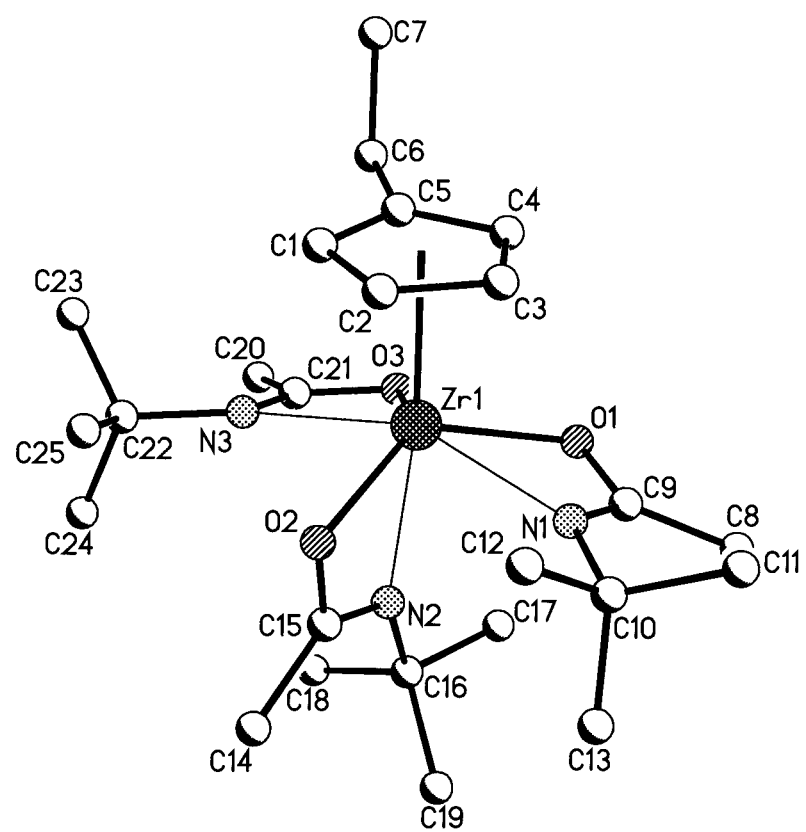
FIG. 5. Drawing representative of the crystal structure of tris-(N-tert-butylacetamidate)ethylcyclopentadienyl zirconium showing bi-dentate binding mode for the amidate ligand, mode (a).

To a suspension of 1.42 g (11.86 mmol) N-tert-butylacetamidate lithium salt in 20 mL of THF at −40° C. was added 2.07 g (5.93 mmol) of bis(ethylcyclopentadienyl)zirconium dichloride dissolved in THF drop wise. The resulting reaction mixture was warmed to room temperature and stirred for 16 hours. The reaction was then refluxed for an additional 16 hours. Upon completion, volatiles were removed under vacuum yielding a waxy beige solid. This solid was extracted with hexanes and filtered yielding 0.36 g of an off white solid reminiscent of lithium chloride salt. The filtrate was removed of hexanes by vacuum to yield 3.05 g of a viscous brown oil. Sublimation of the crude product yielded a yellow solid that was recrystallized in hexanes. The yield was 59% for sublimed material. Elemental analysis: calculated for $C_{25}H_{45}N_3O_3Zr$: C, 56.99; N, 7.98, H, 8.61. Found: C, 55.30; N, 7.91; H, 9.04. $^1$H-NMR (500 MHz, $C_6D_6$) δ (ppm): 6.34 (t, 2H), 6.09 (b, 2H), 2.79 (q, 2H), 1.80, 1.76 (two s, 9H), 1.34 (t, 3H), 1.28, 1.22 (two s, 27H). The crystal structure shown in FIG. 5 indicates that the ethylcyclopentadienyl group is coordinated in $\eta^5$ fashion while the three N-tert-butylacetamidates coordinate as bidentate ligands. TGA analysis indicates a melting point at 170° C. and a 12.93% residual mass.

EXAMPLE 10

Synthesis of tris(N-methylacetamidate)ethylcyclopentadienyl Zirconium

To a suspension of 0.60 g (7.46 mmol) of N-methylacetamidate lithium salt in 20 mL of THF at −40° C. was added a solution of 1.30 g (3.73 mmol) of bis(ethylcyclopentadienyl) zirconium dichloride dissolved in 10 mL of THF drop-wise. The reaction mixture was refluxed for 16 hours, after which all volatiles were removed under vacuum. A tan colored foam was isolated, that was in turn extracted with hexanes and filtered. The filtrate was pumped down under vacuum to an amber colored viscous oil weighing 1.42 g.

EXAMPLE 11

Synthesis of N[(2-(dimethylamino)ethyl]acetamide

To a solution of 13.54 g (153.62 mmol) 3-(dimethylamino) ethylamine in 100 mL of THF at −40° C. was added 6.03 g (76.81 mmol) of acetyl chloride drop-wise. The reaction was stirred at −40° C. for 20 minutes, after which it was warmed to room temperature. 10.71 mL (76.81 mmol) of triethylamine was added and the resulting suspension was left to stir for the extent of 16 hours. After stirring for the amount of time specified, the suspension was filtered, yielding 9.12 g of salt. The filtrate was then pumped under vacuum to a yellow oil weighing 11.21 g. Purification by vacuum distillation yielded a clear liquid weighing 8.67 g of 99% purity based upon GC analysis. The yield was 87%. $^1$H-NMR (500 MHz, $C_6D_6$) δ (ppm): 5.60 (b, 1H), 3.24 (q, 2H), 2.02 (t, 2H), 1.91 (s, 6H), 1.58 (s, 3H).

EXAMPLE 12

Synthesis of N[(2-(dimethylamino)ethyl]acetamidate)tris(ethoxy) Titanium

To a suspension of 1.00 g (7.35 mmol) of N[(2-(dimethylamino)ethyl]acetamidate lithium salt in 20 mL of THF at −78° C. was added a solution of 1.61 g (7.35 mmol) of tris-ethoxy titanium chloride in 10 mL of THF drop-wise. The reaction mixture was allowed to slowly warm to room temperature and then refluxed for the extent of 16 hours. The resulting dark burgundy red solution was pumped under vacuum to remove all volatiles. A brown foam was isolated, that was extracted with a mixture of 1:5 by volume of THF to hexanes. A light beige solid was filtered off, being reminiscent of lithium chloride salt. The filtrate was pumped down under vacuum to isolate 1.36 g of a red-brown foam. Purification was carried out by sublimation, and an off-white waxy solid was collected from the sublimer cold finger. TGA analysis indicates a melting point at 76° C. and a residual mass of 11.89%.

EXAMPLE 13

Synthesis of (N-(tert-butyl)(tert-butyl)amidate)tris (ethoxy) Titanium

To a suspension of 1.00 g (6.13 mmol) of (N-(tert-butyl) (tert-butyl)amidate lithium salt in 30 mL of THF at −78° C. was added a solution of 1.34 g (6.13 mmol) of tris-ethoxy titanium chloride in 10 mL of THF drop-wise. The reaction mixture was slowly warmed to room temperature and refluxed for the extent of 16 hours. Upon completion, all volatiles were removed under vacuum to form a yellow waxy solid. Extraction was carried out with hexanes and 0.22 g of LiCl was filtered off. The filtrate was pumped down under vacuum to yield 1.62 g of a yellow waxy solid. Analysis by TGA indicates a melting point at 85° C. and a residual mass of 6.92%.

EXAMPLE 14

Synthesis of (N-tert-butylacetamidate)tris(ethoxy) Titanium Dimer

Figure 6:
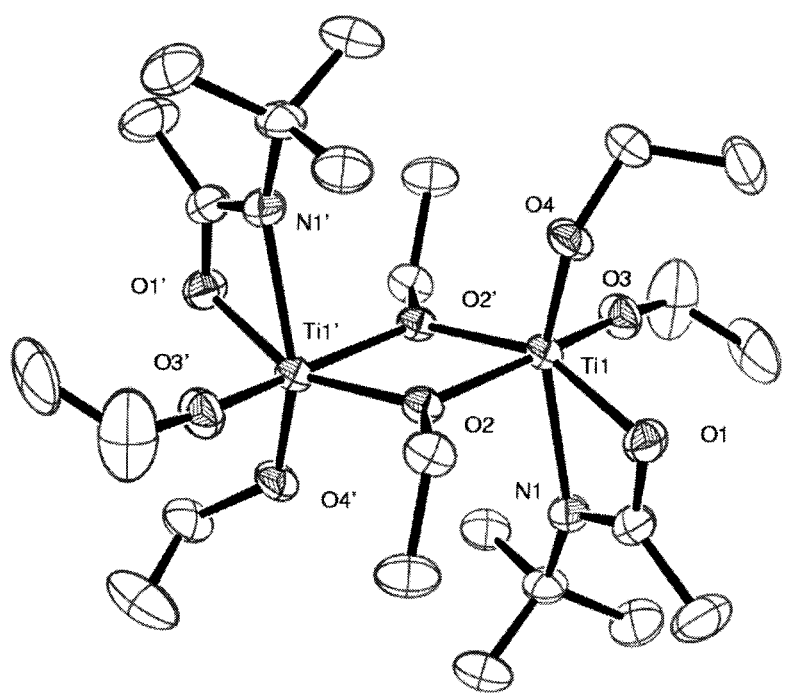
FIG. 6. Drawing representative of the the crystal structure of (N-tert-butylacetamidate)tris(ethoxy) titanium dimer showing bi-dentate binding mode for the amidate ligand, mode (a).

To a suspension of 0.75 g (6.24 mmol) N-tert-butylacetamidate lithium salt in 20 mL of THF at −78° C. purged with argon was added 1.36 g (6.24 mmol) of tris-ethoxy titanium chloride dissolved in THF drop wise. The resulting reaction mixture was warmed to room temperature and stirred for 48 hours. Upon completion, volatiles were removed under vacuum yielding an off-white foam. This in turn was suspended in hexanes and filtered, yielding 0.32 g of a white solid, reminiscent of lithium chloride salt. The filtrate was removed of hexanes by vacuum to yield 1.70 g of a light yellow waxy solid. The yield was 92% for crude product. Elemental analysis: calculated for $C_{24}H_{54}N_2O_8Ti_2$: C, 48.49; N, 4.71, H, 9.16. Found: C, 45.37; N, 4.66; H, 8.78. $^1$H-NMR (500 MHz, $C_6D_6$) δ (ppm): 4.60 (q, $OCH_2CH_3$), 4.52 (b, $OCH_2CH_3$), 1.90 (b, $CH_3$), 1.80 (s, $CH_3$), 1.36 (b, $OCH_2CH_3$), 1.31 (t, $OCH_2CH_3$), 1.27 (s, $C(CH_3)_3$). FIG. 6 shows the crystal structure of the dimer $Ti_2(EtO)_6(MeC(O) NtBu)_2$ where the N-t-butylacetamidates coordinate as terminal bidentate ligands. The two titaniums are bridged by two ethoxy groups, while the remaining four ethoxy groups are terminal, two for each titanium. TGA analysis indicates a melting point of 69° C. and a residual mass of 5.75%.

EXAMPLE 15

Synthesis of bis(N-tert-butylacetamidate)bis(ethoxy) Titanium

To a suspension of 1.31 (10.92 mmol) N-tert-butylacetamidate lithium salt in 20 mL of THF at −40° C. was added 1.14 g (5.46 mmol) bis-ethoxy bis-chloro titanium via solid addition funnel, slowly. The resulting burgundy colored solution became a light tan after approximately 30 minutes. The reaction mixture was refluxed for 16 hours. Upon completion, volatiles were removed under vacuum, yielding an olive green waxy solid. This in turn was suspended in hexanes and filtered yielding 0.46 g of a white solid, reminiscent of lithium chloride salt. The filtrate was removed of hexanes by vacuum to yield a viscous olive green oil weighing 1.86 g. The yield was 93% for crude product. Purification was carried out by vacuum distillation by heating at 130° C. under 200 mTorr vacuum to transfer over a lime green oil in 70% yield. TGA analysis indicates a residual mass of 9.71%. $^1$H-NMR (500 MHz, $C_6D_6$) δ (ppm): 4.60 (q, $OCH_2CH_3$), 1.80 (s, $CH_3$), 1.31 (t, $OCH_2CH_3$), 1.26 (s, $C(CH_3)_3$).

EXAMPLE 16

Synthesis of (N-tert-butylacetamidate)tris(isopropoxy) Titanium

To a suspension of 0.92 g (7.68 mmol) N-tert-butylacetamidate lithium salt in 30 mL of THF at −40° C. was added 2.00 g (7.68 mmol) of tris-isopropoxy titanium chloride dissolved in 10 mL of THF drop wise. The resulting reaction mixture was warmed to room temperature and stirred for 16 hours. Afterward, it was heated at reflux for several hours. Upon completion, volatiles were removed under vacuum, yielding a waxy off-white solid. This in turn was suspended in hexanes and filtered, yielding 0.30 g of a white solid, reminiscent of lithium chloride salt. The filtrate was removed of hexanes by vacuum to yield 2.55 g of an off-white oily solid. The yield was 98% for crude product. TGA analysis indicates a melting point of 40° C. and a residual mass of 1.04%. $^1$H-NMR (500 MHz, $C_6D_6$) δ (ppm): 5.06-4.51 (two m, OCH$(CH_3)_2$), 4.90 (b, $OCH(CH_3)_2$), 1.79-1.73 (two s, $CH_3$), 1.37-1.27 (two d, $OCH(CH_3)_2$), 1.35 (b, $OCH(CH_3)_2$), 1.30-1.26 (two s, $C(CH_3)_3$).

EXAMPLE 17

Synthesis of bis(N-tert-butylacetamidate)bis(isopropoxy) Titanium

To a suspension of 1.02 (8.49 mmol) N-tert-butylacetamidate lithium salt in 10 mL of THF at −40° C. was added 1.01 g (4.25 mmol) bis-isopropoxy bis-chloro titanium via solid addition funnel slowly. The resulting reaction mixture was refluxed for 16 hours. Upon completion, volatiles were removed under vacuum and residual crude material was suspended in hexanes and filtered yielding 0.39 g of a white solid, reminiscent of lithium chloride salt. The filtrate was removed of hexanes by vacuum to yield a viscous oil weighing 1.63 g. The yield was 97% for crude product. $^1$H-NMR (500 MHz, $C_6D_6$) δ (ppm): 5.04 (m, $OCH(CH_3)_2$), 1.79 (s, $CH_3$), 1.37 (d, $OCH(CH_3)_2$), 1.28 (s, $C(CH_3)_3$).

EXAMPLE 18

ALD Deposition of Titanium Oxide Films using (N-(tert-butyl)(tert-butyl)amidate)tris(dimethylamido) Titanium This example described a typical ALD deposition of titanium oxide using ozone and titanium precursor (N-(tert-butyl)(tert-butyl)amidate)tris(dimethylamido) titanium. The deposition temperature was at 200° C., and bubbler was held at 65° C. to deliver the titanium precursor. The deposition chamber pressure was around 1.5 Torr, depending upon the gas flow rates. One cycle of the ALD of titanium oxide consisted of 4 steps:

1. Titanium precursor pulse: Introducing Ti precursor vapor to the deposition chamber during which titanium precursor is chemisorbed on the surface,
2. Ar purge: purging away any excess of titanium precursor with Ar;
3. Ozone pulse: introducing ozone into the deposition chamber to react with chemisorbed titanium precursor on the heated substrate; and,
4. Ar purge: purging away any unreacted ozone and by-products with Ar.

Figure 7:
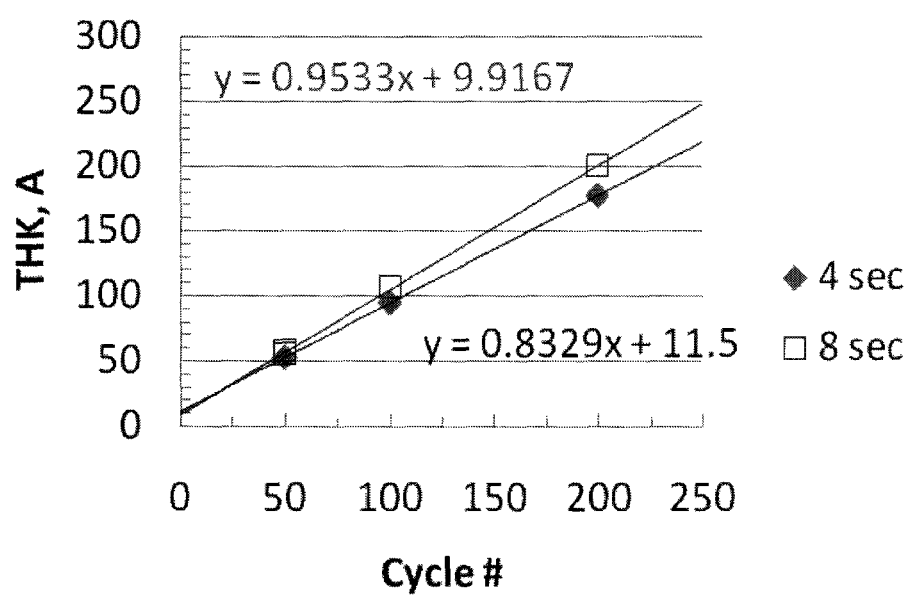
FIG. 7. The dependence of titanium oxide film thickness (THK in Angstroms (Å)) on the number of cycles and cycle time duration in ALD process using ozone and (N-(tert-butyl)(tert-butyl)amidate)tris(dimethylamido) titanium.

In this example, titanium oxide films were deposited, showing the dependence of the thickness of titanium oxide film on the number of cycles and cycle time duration. The titanium precursor cycle was 4 and 8 seconds, the Ar purge time after Sr pulse was 10 seconds, the ozone pulse time was 5 seconds, and the Ar purge time after ozone pulse was 10 seconds. The results are depicted in FIG. 7 showing linear dependence of film thickness on the number of cycles and only small difference in ALD rate between 4 and 8 sec pulses of titanium precursor. The ALD deposition rate of titanium oxide using ozone and titanium precursor (N-(tert-butyl)(tert-butyl)amidate)tris(dimethylamido) titanium at 200° C. was ~0.9 A/cycle.

The invention claimed is:

1. A volatile amidate metal complex represented by the following Formula I:

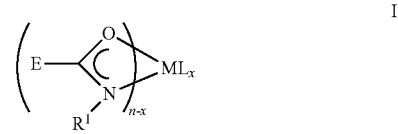

where M is selected from the Group 2 to Group 15 metals; $R^1$ is selected from the group consisting of linear or branched alkyl group containing 1 to 5 carbon atom, linear or branched alkoxyalkyl, and linear or branched aminoalkyl; E is $R^2$ or $NR^3R^4$, where $R^2$, $R^3$, $R^4$ are independently selected from the group consisting of linear or branched alkyl group containing 1-6 carbon atoms, cyclic alkyl group containing 4-6 carbon atoms, and an aromatic group containing 6-12 carbon atoms; L is an anionic ligand independently selected from the group consisting of alkoxy, amino, diketonate, ketoiminate, diiminate, cyclopentadienyl, alkyl substituted cyclopentadienyl, alkoxysubstituted cyclopentadienyl, aminosubsitituted cyclopentadienyl, pyrrolyl, alkyl substituted pyrrolyl, alkoxysubstituted pyrrolyl, and aminosubsitituted pyrrolyl; n is the oxidation state of M; and x is 1 to n−1.

2. The amidate metal complex of claim 1 having vapor pressure above 0.5 torr at a temperature less than 200° C.

3. The amidate metal complex of claim 1 wherein M is selected from the group consisting of titanium, zirconium, hafnium, vanadium, niobium, tantalum, chromium, molybdenum, tungsten, lanthanide metals, calcium, strontium, barium, manganese, cobalt, nickel, iron and combination thereof.

4. The amidate metal complex of claim 1 represented by the Formula II

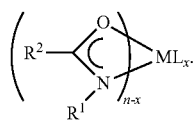

5. The amidate metal complex of claim 1 represented by the Formula III:

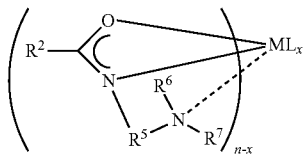

wherein M is selected from the group consisting of titanium, zirconium, hafnium, vanadium, niobium, tantalum, chromium, molybdenum, tungsten, lanthanide metals, calcium, strontium, barium, manganese, cobalt, nickel, iron and combination thereof; where $R^2$, $R^6$ and $R^7$ are independently selected from the group consisting of linear or branched alkyl group containing 1-6 carbon atoms, cyclic alkyl groups of 4-6 carbon atoms and aromatic groups of 6-12 carbon atoms; $R^5$ is $C_{2-3}$ linear or branched alkylene bridge; L is an anionic ligand independently selected from the group consisting of alkoxy, amino, diketonate, ketoiminate, diiminate, cyclopentadienyl, alkyl substituted cyclopentadienyl, alkoxysubstituted cyclopentadienyl, aminosubsitituted cyclopentadienyl, pyrrolyl, alkyl substituted pyrrolyl, alkoxysubstituted pyrrolyl, and aminosubsitituted pyrrolyl; n is the oxidation state of M; and x is 0 to n−1.

6. The metal complex of claim 1 represented by the Formula IV:

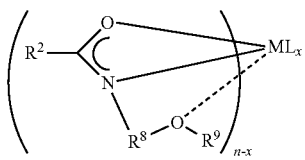

wherein M is selected from the group consisting of titanium, zirconium, hafnium, vanadium, niobium, tantalum, chromium, molybdenum, tungsten, lanthanide metals, calcium, strontium, barium, manganese, cobalt, nickel, iron and combination thereof; where $R^2$ and $R^9$ are independently selected from the group consisting of linear or branched alkyl group containing 1-6 carbon atoms, cyclic alkyl groups of 4-6 carbon atoms and aromatic groups of 6-12 carbon atoms; $R^8$ is $C_{2-3}$ linear or branched alkylene bridge; L is an anionic ligand independently selected from the group consisting of alkoxy, amino, diketonate, ketoiminate, diiminate, cyclopentadienyl, alkyl substituted cyclopentadienyl, alkoxysubstituted cyclopentadienyl, aminosubsitituted cyclopentadienyl, pyrrolyl, alkyl substituted pyrrolyl, alkoxysubstituted pyrrolyl, and aminosubsitituted pyrrolyl; n is the oxidation state of M; and x is 0 to n−1.

7. The metal complex of claim 1 represented by the Formula V:

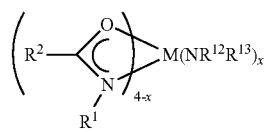

where M is selected from the group consisting of Ti, Zr, and Hf; $R^1$ and $R^2$ are independently selected from the group consisting of linear or branched alkyl group containing 1 to 6 carbon atom, linear or branched alkoxyalkyl, linear or branched aminoalkyl; $R^{12}$, $R^{13}$ are independently selected from the group consisting of linear, cyclic or branched alkyl group containing 1-6 carbon atoms; x is 0, 1, 2 or 3.

8. The metal complex of claim 7 having the following structure where Me is methyl and Bu$^t$ is tert-butyl;

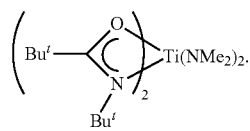

9. The metal complex of claim 7 having the following structure where Et is ethyl, Pr$^i$ is iso-propyl and Bu$^t$ is tert-butyl;

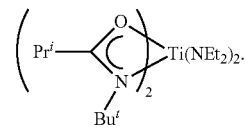

10. The metal complex of claim 7 having the following structure where Me is methyl and Bu$^t$ is tert-butyl;

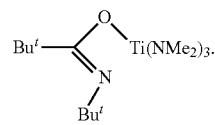

11. The metal complex of claim 7 having the following structure where Me is methyl, Et is ethyl and Bu$^t$ is tert-butyl;

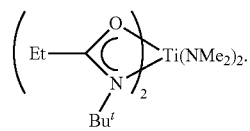

12. The metal complex of claim 7 having the following structure where Me is methyl, Et is ethyl and Bu$^t$ is tert-butyl;

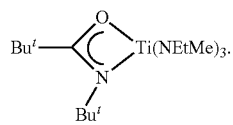

13. The metal complex of claim 7 having the following structure where Me is methyl and Bu$^t$ is tert-butyl;

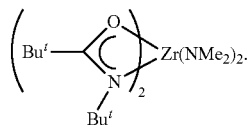

14. The metal complex of claim 1 represented by the Formula VI:

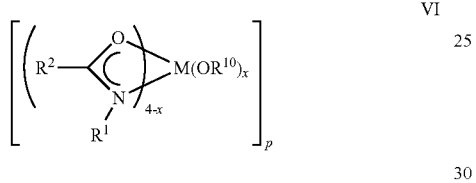

where M is selected from the group consisting of Ti, Zr, and Hf; $R^2$ and $R^{10}$ are independently selected from the group consisting of linear or branched alkyl group containing 1 to 6 carbon atom; $R^1$ is selected from the group consisting of linear or branched alkyl group containing 1 to 5 carbon atom; x is 0, 1, 2 or 3; p=1 or 2.

15. The metal complex of claim 12 wherein $R^{1-2}$ and $R^{10}$ are independently selected from the group consisting of methyl, ethyl, n-propyl, iso-propyl, n-butyl, iso-butyl, sec-butyl, and tert-butyl; x is 1 or 2; p=1 or 2.

16. The metal complex of claim 1 represented by Formula VII:

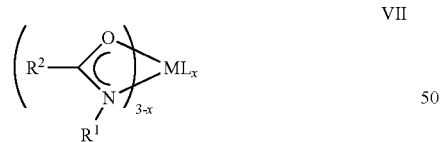

where M is selected from the group consisting of scandium, yttrium, lanthanide metals and mixtures thereof; $R^1$ and $R^2$ are independently selected from the group consisting of linear or branched alkyl group containing 1 to 6 carbon atom; L is an anionic ligand independently selected from alkoxy, amido, diketonate, ketoiminate, diiminate, cyclopentadienyl, alkyl substituted cyclopentadienyl, alkoxysubstituted cyclopentadienyl, aminosubstituted cyclopentadienyl, pyrrolyl, alkyl substituted pyrrolyl, alkoxysubstituted pyrrolyl, and aminosubstituted pyrrolyl; x is 0, 1 or 2.

17. The metal complex of claim 1 represented by Formula VIII

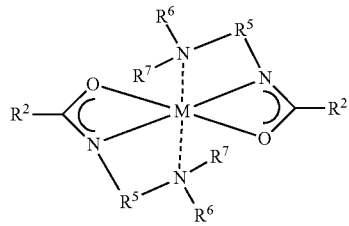

where M is selected from the group consisting of calcium, strontium and barium; where $R^2$, $R^6$ and $R^7$ are independently selected from the group consisting of linear or branched alkyl group containing 1-6 carbon atoms, cyclic alkyl groups of 4-6 carbon atoms, aromatic groups of 6-12 carbon atoms; and $R^5$ is a linear or branched alkylene bridge, preferably ethylene or propylene group.

18. The metal complex of claim 1 represented by Formula IX:

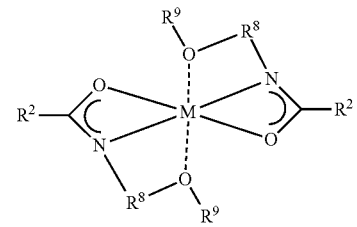

where M is selected from the group consisting of calcium, strontium and barium; where $R^2$ and $R^9$ are independently selected from the group consisting of linear or branched alkyl group containing 1-6 carbon atoms, cyclicalkyl groups of 4-6 carbon atoms and aromatic groups of 6-12 carbon atoms; and $R^8$ is a linear or branched alkylene bridge, preferably ethylene or propylene group.

19. The metal complex of claim 1 represented by Formula X:

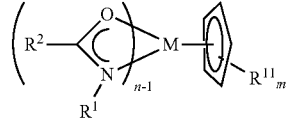

where M is selected from the group consisting of titanium, zirconium, hafnium, vanadium, niobium, tantalum, chromium, molybdenum, tungsten, lanthanide metals, calcium, strontium, barium, manganese, cobalt, nickel, iron and combination thereof; $R^{1, 2 \& 11}$ are independently selected from the group consisting of linear or branched alkyl group containing 1 to 6 carbon atom, linear or branched alkoxyalkyl, and linear or branched aminoalkyl; m=0, 1, 2, 3, 4, 5; and n is the oxidation state of M.

20. The metal complex of claim 19 wherein M=Zr; $R^{1-2}$ and $R^{11}$ are independently selected from the group consisting of methyl (Me), ethyl (Et), n-propyl, iso-propyl (Pr$^i$) n-butyl, iso-butyl, sec-butyl, and tert-butyl (Bu$^t$).

21. A method for depositing a metal-containing film on a substrate comprising;
(a) providing a amidate metal complex represented by the following Formula I:

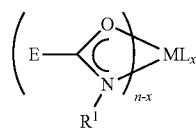

where M is selected from the Group 2 to Group 15 metal; $R^1$ is selected from the group consisting of linear or branched alkyl group containing 1 to 5 carbon atom, linear or branched alkoxyalkyl, linear or branched aminoalkyl; E is $R^2$ or $NR^3R^4$, where $R^2$, $R^3$, $R^4$ are independently selected from the group consisting of linear, cyclic or branched alkyl group containing 1-6 carbon atoms, or an aromatic group; L is an anionic ligand independently selected from alkoxy, amino, diketonate, ketoiminate, diiminate, cyclopentadienyl, alkyl substituted cyclopentadienyl, alkoxysubstituted cyclopentadienyl, aminosubsitituted cyclopentadienyl, pyrrolyl, alkyl substituted pyrrolyl, alkoxysubstituted pyrrolyl, and aminosubsitituted pyrrolyl; n is the oxidation state of M; and x is 1 to n−1;
(b) providing a substrate; and,
(c) depositing a metal containing film from the amidate metal complex using a process selected from the group consisting of cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, low energy CVD (LECVD), plasma enhanced ALD (PEALD), and plasma enhanced cyclic CVD (PECCVD).

22. The method of claim 21 where the temperature is in the range of 200 to 500° C.

23. The method of claim 21 including co-deposition of metal from a metal complex selected from the group consisting of tetrakis(dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino)bis(ethylmethylamino)tungsten, bis(2,2,6,6-tetramethyl-3,5-heptanedionato)strontium, bis(2,2,6,6-tetramethyl-3,5-heptanedionato)barium, $M(R_nC_5H_{5-n})_2$, wherein n=1-5, R is selected from linear or branched $C_{1-6}$ alkyls; $M(R_nC_4H_{4-n})_2$, wherein n=2-4, R is selected from linear or branched $C_{1-6}$ alkyls; $M(R_nN_2H_{3-n})_2$, where n=2-3, R is selected from linear or branched $C_{1-6}$ alkyls, and combinations thereof.

24. The method of claim 21 including providing an oxygen source selected from the group consisting of water ($H_2O$) (e.g., deionized water, purifier water, distilled water), water plasma, oxygen ($O_2$), oxygen plasma, ozone ($O_3$), NO, $NO_2$, carbon monoxide (CO), carbon dioxide ($CO_2$) and combinations thereof.

25. The method of claim 21 including providing a nitrogen source selected from the group consisting of NO, $NO_2$, ammonia, hydrazine, monoalkylhydrazine, dialkylhydrazine, and combinations thereof.

26. The method of claim 21 including providing an energy source selected from the group consisting of thermal, plasma, pulsed plasma, helicon plasma, high density plasma, inductively coupled plasma, X-ray, e-beam, photon, remote plasma, secondary RF frequency and combinations thereof.

27. The method of claim 21 including the steps comprising;
a. introducing a metal-containing precursor in a vapor state into a reaction chamber and chemisorbing the metal-containing precursor onto a substrate which is heated;
b. purging away the unreacted metal-containing precursor;
c. introducing an oxygen source onto the heated substrate to react with the sorbed metal-containing precursor;
d. purging away the unreacted oxygen source; and
e. the steps are repeated until a desire thickness of metal-containing film is achieved.

* * * * *